US00PP18767P2

(12) United States Plant Patent
von Rundstedt

(10) Patent No.: US PP18,767 P2
(45) Date of Patent: Apr. 29, 2008

(54) ***GENTIANA* PLANT NAMED 'ALPINE SUCCESS BLUE 05'**

(50) Latin Name: *Gentiana cruciata×scabra*
Varietal Denomination: Alpine Success Blue 05

(75) Inventor: Friederike von Rundstedt, Bremen (DE)

(73) Assignee: Wolfgang Bock Pflanzenexport KG, Bremen (DE)

( * ) Notice: Subject to any disclaimer, the term of this patent is extended or adjusted under 35 U.S.C. 154(b) by 0 days.

(21) Appl. No.: 11/648,869

(22) Filed: Dec. 29, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Gentiana* plant named 'Alpine Success Blue 05', characterized by its upright, outwardly spreading, uniform and compact plant habit; vigorous growth habit; freely branching habit; early and freely flowering habit; large intense blue-colored flowers; and long flowering period.

3 Drawing Sheets

Botanical designation: *Gentiana cruciata×scabra.*
Cultivar denomination: 'Alpine Success Blue 05'.

BACKGROUND OF THE INVENTION

The present invention relates to a new and distinct cultivar of *Gentiana,* botanically known as *Gentiana cruciata× scabra* and hereinafter referred to by the name 'Alpine Success Blue 05'.

The new *Gentiana* is a product of a planned breeding program conducted by the Inventor in Bremen, Germany. The objective of the breeding program is to create new freely-branching *Gentiana* cultivars with early and freely flowering habit and larger more intensely blue-colored flowers.

The new *Gentiana* originated from a cross-pollination made by the Inventor in September, 2003, of an unnamed selection of *Gentiana cruciata×scabra,* not patented, as the female, or seed, parent with the *Gentiana cruciata×scabra* cultivar Alpine Success Blue 01, not patented, as the male, or pollen, parent. The new *Gentiana* was discovered and selected by the Inventor as a single flowering plant from within the progeny of the stated cross-pollination grown in a controlled environment in Bremen, Germany during the late spring in 2004.

Asexual reproduction of the new cultivar by tissue culture in Bremen, Germany, since 2004, has shown that the unique features of this new *Gentiana* are stable and reproduced true to type in successive generations.

SUMMARY OF THE INVENTION

Plants of the cultivar Alpine Success Blue 05 have not been observed under all possible environmental conditions. The phenotype may vary somewhat with variations in environment such as temperature and light intensity without, however, any variance in genotype.

The following traits have been repeatedly observed and are determined to be the unique characteristics of 'Alpine Success Blue 05'. These characteristics in combination distinguish 'Alpine Success Blue 05' as a new and distinct cultivar:

1. Upright, outwardly spreading, uniform and compact plant habit.
2. Vigorous growth habit.
3. Freely branching habit.
4. Early and freely flowering habit.
5. Large intense blue-colored flowers.
6. Long flowering period.

Plants of the new *Gentiana* differ from plants of the female parent selection in the following characteristics:

1. Plants of the new *Gentiana* are taller than plants of the female parent selection.
2. Leaves of plants of the new *Gentiana* are longer and more tapering at the apex than leaves of plants of the female parent selection.
3. Plants of the new *Gentiana* have larger flowers than plants of the female parent selection.
4. Plants of the new *Gentiana* and the female parent selection differ in flower color as flower color of plants of the female parent selection is red purple in color.
5. Plants of the new *Gentiana* flower from May to September in Bremen, Germany whereas plants of the female parent selection flower from August to November in Bremen, Germany.

Plants of the new *Gentiana* differ from plants of the male parent, the cultivar Alpine Success Blue 01, in the following characteristics:

1. Plants of the new *Gentiana* are larger than plants of the cultivar Alpine Success Blue 01.
2. Plants of the new *Gentiana* are more freely branching than plants of the cultivar Alpine Success Blue 01.
3. Leaves of plants of the new *Gentiana* are more tapering at the apex than leaves of plants of the cultivar Alpine Success Blue 01.
4. Plants of the new *Gentiana* have larger flowers than plants of the cultivar Alpine Success Blue 01.

5. Plants of the new *Gentiana* and the cultivar Alpine Success Blue 01 differ in flower color as flower color of plants of the cultivar Alpine Success Blue 01 is lighter blue in color.
6. Plants of the new *Gentiana* flower from May to September in Bremen, Germany whereas plants of the cultivar Alpine Success Blue 01 flower from September to November in Bremen, Germany.

Plants of the new *Gentiana* can be compared to plants of the *Gentiana makinoi* cultivar Marsha, disclosed in U.S. Plant Pat. No. 16,562. In side-by-side comparisons conducted in Bremen, Germany, plants of the new *Gentiana* differed from plants of the cultivar Marsha in the following characteristics:

1. Plants of the new *Gentiana* were smaller than plants of the cultivar Marsha.
2. Plants of the new *Gentiana* were more freely branching than plants of the cultivar Marsha.
3. Plants of the new *Gentiana* had smaller leaves than plants of the cultivar Marsha.
4. Plants of the new *Gentiana* had larger flowers than plants of the cultivar Marsha.
5. Plants of the new *Gentiana* and the cultivar Marsha differed in flower color.
6. Plants of the new *Gentiana* flowered from May to September in Bremen, Germany whereas plants of the cultivar Marsha flowered from July to early September in Bremen, Germany.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Gentiana.*

The photograph on the first sheet comprises a side perspective view of typical a flowering plant of 'Alpine Success Blue 05' grown in a container.

The photograph on the second sheet is a close-up view of typical flower of 'Alpine Success Blue 05'.

The photo on the third sheet is a close-up view of the upper surface of a typical leaf of 'Alpine Success Blue 05'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the spring and summer in a glass-covered greenhouse in Bremen, Germany for about 18 weeks. During the production of the plants, day temperatures ranged from 20° C. to 25° C., night temperatures ranged from 18° C. to 20° C. and light levels were about 20 kilolux.

Botanical classification: *Gentiana cruciata×scabra* cultivar Alpine Success Blue 05.

Parentage:

*Female parent.*—Unnamed selection of *Gentiana cruciata×scabra,* not patented.

*Male parent.*—*Gentiana cruciata×scabra* cultivar Alpine Success Blue 01, not patented.

Propagation:

*Type.*—Tissue culture.

*Time to initiate roots, summer.*—About 18 days at 23° C.

*Time to initiate roots, winter.*—About 21 days at 21° C.

*Time to produce a rooted young plant, summer.*—About six weeks at 23° C.

*Time to produce a rooted young plant, winter.*—About seven weeks at 21° C.

*Root description.*—Fine; 155D in color.

*Rooting habit.*—Freely branching; dense.

Plant description:

*Form.*—Perennial potted plant. Upright, outwardly spreading, uniform and compact plant habit; broad bowl-like inverted triangle; freely basal branching habit; about 25 branches develop per plant. Vigorous growth habit. Campanulate flowers arranged in terminal and axillary clusters.

*Plant height.*—About 20 cm to 25 cm.

*Plant width.*—About 20 cm to 25 cm.

*Lateral branch description.*—Length: About 4 cm to 6 cm. Diameter: About 2 cm to 4 cm. Internode length: About 3 mm to 5 mm. Strength: Strong. Aspect: Upright to outwardly spreading. Texture: Smooth, glabrous. Color: 144C tinted with 183A to 183B.

Foliage description:

*Arrangement.*—Opposite, simple; sessile.

*Length.*—About 5 cm.

*Width.*—About 5 mm to 10 mm.

*Shape.*—Lanceolate.

*Apex.*—Acute.

*Base.*—Cuneate.

*Margin.*—Entire.

*Texture, upper and lower surfaces.*—Smooth, glabrous.

*Venation pattern.*—Parallel.

*Color.*—Developing and fully expanded foliage, upper surface: 137A; venation, slightly brighter than 137A. Developing and fully expanded foliage, lower surface: 144A; slightly darker than 144A.

Flower description:

*Flower arrangement and shape.*—Single campanulate flowers arranged in terminal and axillary clusters; flowers face mostly upright. Freely flowering habit, about five flower buds and open flowers per branch.

*Natural flowering season.*—Early and continuous flowering habit from May to September in Bremen, Germany.

*Flower longevity on the plant.*—About 24 days; flowers persistent.

*Fragrance.*—None detected.

*Flower buds.*—Length: About 4.5 cm to 5 cm. Diameter: About 1.3 cm. Shape: Oval to oblong; tapering towards the apex. Color: 89A; towards the apex, 143A to 143B.

*Flower diameter.*—About 3 cm to 3.5 cm.

*Flower depth (height).*—About 5 cm.

*Petals.*—Arrangement: Five in a single whorl; fused. Length: About 4 cm to 5 cm. Width: About 1 cm. Shape: Oblong. Apex: Acute. Margin: Serrate. Texture, upper and lower surfaces: Smooth, glabrous; silky. Color: When opening and fully opened, upper surface: 104A; color becoming closer to 96B with development. When opening and fully opened, lower surface: 104A to 104B; longitudinal stripes, 95C, becoming closer to 144A to 146B; towards the base, close to 155D.

*Sepals.*—Arrangement: Five in a single whorl; fused. Length: About 2 cm. Width: About 3 mm. Shape: Lanceolate. Apex: Acute. Margin: Entire. Texture, upper and lower surfaces: Smooth, glabrous; silky. Color, upper surface: 137A. Color, lower surface: 144B, tinted with 183A.

*Pedicels.*—Length: About 6 mm. Diameter: About 2 mm. Aspect: About 20° from vertical. Strength: Strong. Texture: Smooth, glabrous. Color: 144B.

*Reproductive organs.*—Stamens: Quantity per flower: Five. Anther shape: Oblong. Anther length: About 3 mm. Anther color: 9C. Pollen amount: Scarce. Pollen color: 11D. Pistils: Quantity per flower: One. Pistil length: About 3 cm. Stigma shape: Decurrent, divided in the center. Stigma color: 1D. Style length: About 2.8 cm. Style color: 145B. Ovary color: 150C to 150D.

*Seed/fruit.*—Seed and fruit production has not been observed.

Disease/pest resistance: Plants of the new *Gentiana* have not been noted to be resistant to pathogens and pests common to *Gentiana*.

Garden performance: Plants of the new *Gentiana* have exhibited good tolerance to rain, wind and temperatures ranging from −25° C. to 30° C.

It is claimed:

1. A new and distinct *Gentiana* plant named 'Alpine Success Blue 05' as illustrated and described.

* * * * *

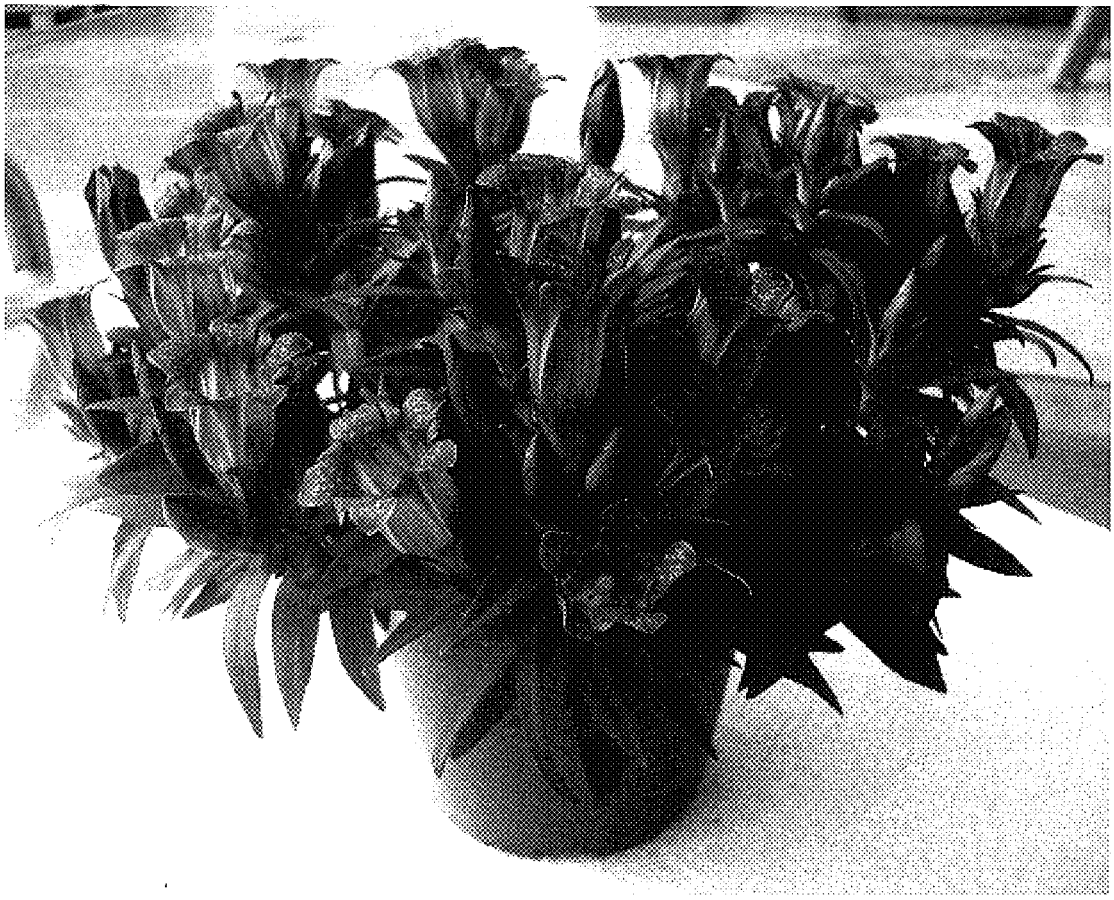

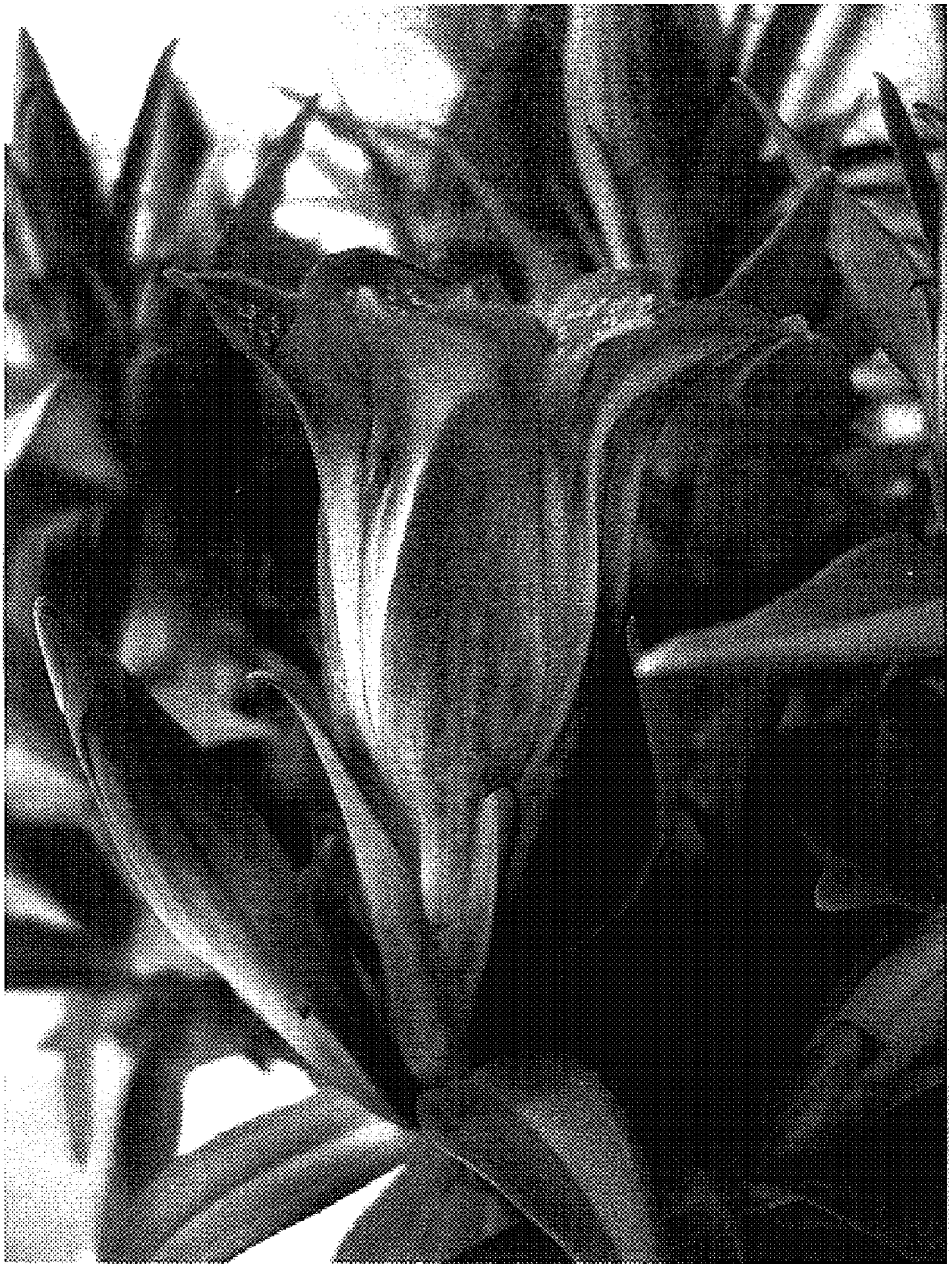

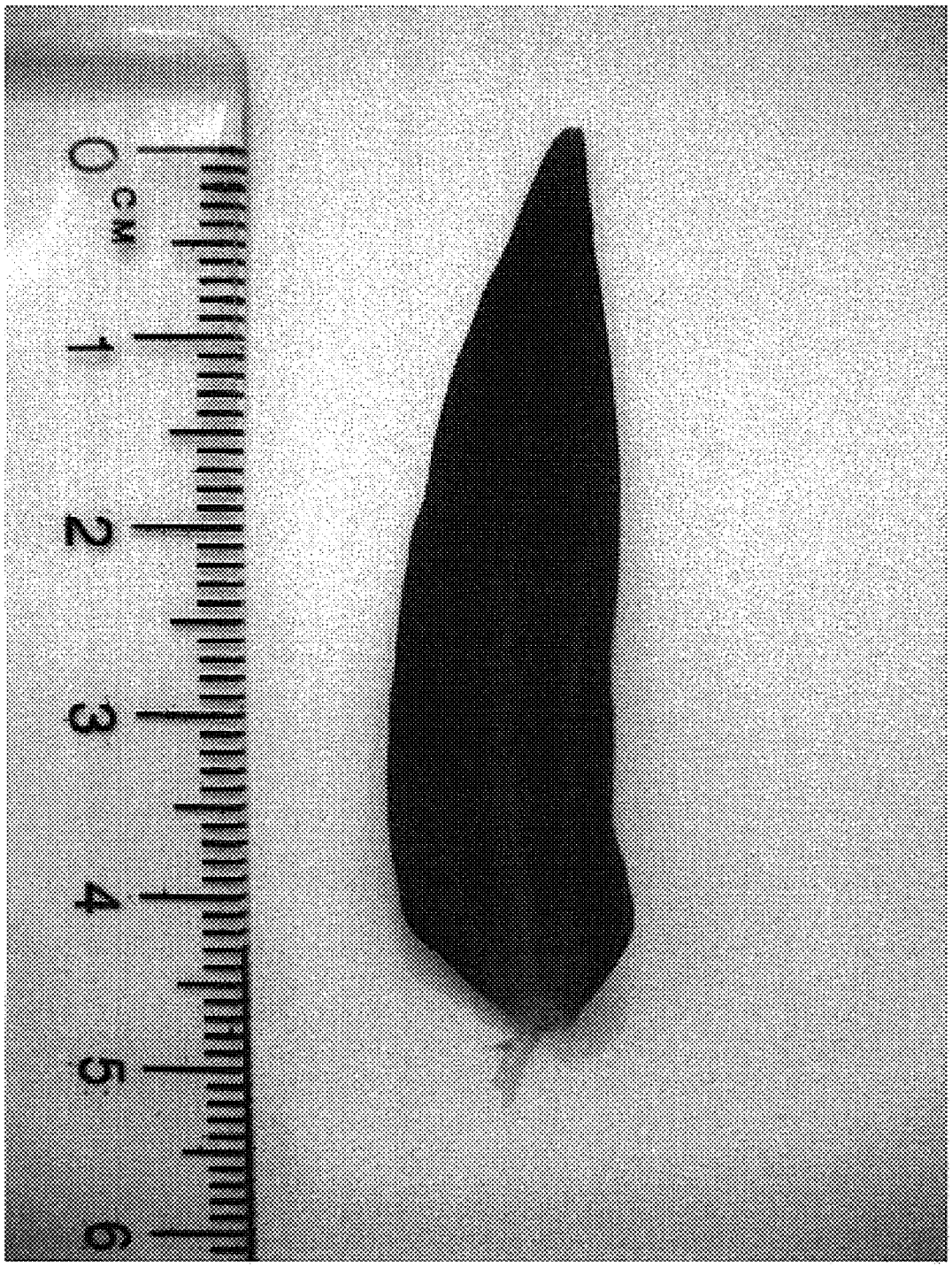
0 cm
1
2
3
4
5
6